(12) United States Patent
Matsuno et al.

(10) Patent No.: US 6,689,576 B2
(45) Date of Patent: Feb. 10, 2004

(54) CHEMILUMINESCENT ASSAY

(75) Inventors: Tatsuki Matsuno, Tokyo (JP); Hiroko Saruta, Tokyo (JP)

(73) Assignee: Fujirebio, Inc., Tokyo (JP)

(*) Notice: Subject to any disclaimer, the term of this patent is extended or adjusted under 35 U.S.C. 154(b) by 147 days.

(21) Appl. No.: 09/749,393

(22) Filed: Dec. 28, 2000

(65) Prior Publication Data

US 2001/0005584 A1 Jun. 28, 2001

(30) Foreign Application Priority Data

Dec. 28, 1999 (JP) .............................. 11-374513
Oct. 2, 2000 (JP) ........................ 2000-301889

(51) Int. Cl.[7] .............................. C12Q 1/42; C12Q 1/54; C12Q 1/00; G01N 33/53
(52) U.S. Cl. ............................. 435/21; 435/14; 435/4; 435/968
(58) Field of Search ................................. 435/21, 14, 4, 435/968

(56) References Cited

U.S. PATENT DOCUMENTS 4,959,182 A * 9/1990 Schaap ......................... 435/21
5,994,073 A * 11/1999 Bronstein et al. .............. 435/6

* cited by examiner

Primary Examiner—Louise N. Leary
(74) Attorney, Agent, or Firm—Birch, Stewart, Kolasch & Birch, LLP (57) ABSTRACT

A method for measuring chemiluminescence by which measurement of chemiluminescence can be carried out efficiently and accurately. In this method, an enzyme reaction of a chemiluminescent substrate in the presence of the enzyme carrying out the enzyme reaction and a chemiluminescence enhancer is conducted further in the presence of a chemiluminescence intensity-adjusting agent; and then the resulting chemiluminescence from the reaction product is measured.

17 Claims, 6 Drawing Sheets

CHEMILUMINESCENT ASSAY

BACKGROUND OF THE INVENTION

I. Field of the Invention

The present invention relates to a chemiluminescent assay by which chemiluminescent assay can be carried out efficiently and accurately. The chemiluminescent assay is especially useful for enzyme immunoassays.

II. Background of the Invention

Chemiluminescent assays enable detection and quantification of target substances in test samples quickly and highly sensitively, so that they are widely used in measuring viruses such as HIV and HCV, and other trace components in the body.

Among the chemiluminescent compounds, 1,2-dioxetanes are drawing attention as chemiluminescent substrates. Various improvements in sensitivity or ease of handling have been made for the chemiluminescent assays in which 1,2-dioxetanes as substrates are subjected to enzyme reactions and the emitted chemiluminescnece is measured.

Studies for promoting sensitivities of chemiluminescent assays have been vigorously made and various chemiluminescence enhancers which increase the intensity of the chemiluminescence so as to promote sensitivity of the assay have been discovered for the chemiluminescent assays using 1,2-dioxetanes as chemiluminescent substrates. A representative example of such a chemiluminescence enhancer is polyvinylbenzyltributylammonium chloride (hereinafter also referred to as "TBQ") (see Japanese Laid-open Patent Application (Kokai) No. 4-124185) and various improvements have been proposed for increasing the intensity of the chemiluminescence in the chemiluminescent assays using TBQ as a chemiluminescent enhancer.

In assay systems using such a chemiluminescence enhancer, when the enzyme concentration is low, the chemiluminescence-enhancing efficiency is extremely high, while when the enzyme concentration exceeds a certain level, the chemiluminescence-enhancing efficiency gradually decreases, so that the relationship between the enzyme concentration and the intensity of the emitted chemiluminescence is not linear or proportional. Therefore, it is difficult to use the calibration curve in the assays, so that measurements of enzyme concentrations could not be carried out efficiently and accurately. No countermeasures for improving the proportionality of the calibration curve have been proposed.

SUMMARY OF THE INVENTION

Accordingly, an object of the present invention is to provide a chemiluminescent assay in which the proportionality between the enzyme concentration and the intensity of the emitted chemiluminescence is increased.

The present inventors intensively studied to discover that the linearity or proportionality between the enzyme concentration and the intensity of the emitted chemiluminescence is increased by making a chemiluminescence intensity-adjusting agent co-exist in the reaction system, thereby completing the present invention.

That is, the present invention provides a chemiluminescent assay comprising subjecting a chemiluminescent substrate to an enzyme reaction in the presence of the enzyme carrying out the enzyme reaction, a chemiluminescence enhancer and a chemiluminescence intensity-adjusting agent; and measuring resulting chemiluminescence from reaction product.

By the present invention, the linearity or proportionality between the enzyme concentration and the intensity of the emitted chemiluminescence in chemiluminescent assays is increased. Therefore, chemiluminescent assays can be carried out more efficiently and more accurately than the known chemiluminescent assays.

BEST MODE FOR CARRYING OUT THE INVENTION

The most characteristic feature of the present invention is the use of the chemiluminescence intensity-adjusting agent. Preferred chemiluminescence intensity-adjusting agents which may be used in the present invention are represented by the following Formula (III):

(III)

(wherein $R^{15}$ represents $C_8$–$C_{22}$ alkyl; $R^{16}$, $R^{17}$ and $R^{18}$ independently represent $C_1$–$C_6$ alkyl or $C_7$–$C_{12}$ aralkyl; and X represents halogen).

In Formula (III), the $C_8$–$C_{22}$ alkyl for $R^{15}$ and the $C_1$–$C_6$ alkyl for $R^{16}$, $R^{17}$ and $R^{18}$ may be straight or branched, and straight alkyl groups are preferred. Among the $C_8$–$C_{22}$ alkyl groups, preferred are $C_{10}$–$C_{18}$ alkyl groups such as lauryl, myristyl, cetyl and stearyl groups. Among the $C_1$–$C_6$ alkyl groups, preferred are $C_1$–$C_3$ alkyl groups, that is, methyl, ethyl and propyl groups. Among the $C_7$–$C_{12}$ aralkyl groups, preferred are those wherein $C_1$–$C_6$ alkyl, preferably straight alkyl, is substituted with phenyl, such as benzyl, phenylethyl and phenylpropyl.

Specific preferred examples of the chemiluminescence intensity-adjusting agents which may be used in the present invention include myristyltrimethylammonium bromide (hereinafter also referred to as "MTAB"), cetyltrimethylammonium bromide (hereinafter also referred to as "CTAB"), lauryltrimethylammonium bromide (hereinafter also referred to as "DTAB"), stearyltrimethylammonium bromide (hereinafter also referred to as "STAB"), myristyltrimethylammonium chloride (hereinafter also referred to as "MTAC") and benzyldimethylmyristylammonium chloride (hereinafter also referred to as "BDMAC"). These chemiluminescence intensity-adjusting agents may be used individually or in combination.

Among these, MTAB is especially preferred since the proportionality between the enzyme concentration and the intensity of the emitted chemiluminescence is high.

The amount of the chemiluminescence intensity-adjusting agent to be used is the amount at which the proportionality between the enzyme concentration and the intensity of the emitted chemiluminescence is significantly increased when compared with the case where the chemiluminescence intensity-adjusting agent is not used, and at which the sensitivity of the chemiluminescent assay is not significantly decreased. If the amount of the chemiluminescence intensity-adjusting agent is too small, the effect to improve the proportionality between the enzyme concentration and the intensity of the emitted chemiluminescence is not obtained. On the other hand, if the amount of the chemiluminescence intensity-adjusting agent is too large, the enhancement of emission of chemiluminescence, which is brought about by the chemiluminescence enhancer, is hindered.

Usually, the weight of the used chemiluminescence intensity-adjusting agent is 1/40 to the same weight of the used chemiluminescence enhancer such as TBQ, more preferably 1/5 to 1/2 of the weight of the used chemiluminescence enhancer.

In the chemiluminescent assay according to the present invention, any chemiluminescent substrate which is used in the conventional chemiluminescent assays may be employed.

A family of preferred chemiluminescent substrates is represented by the following Formula (I):

(I)

(wherein $R^1$ represents hydrogen or halogen; $R^2$ represents $C_1$–$C_6$ alkyl or $C_3$–$C_6$ cycloalkyl; $Ar^1$ represents phenylene or naphthylene; $R^3$ represents a group of the formula —$OPO_3^{2-}.2M^+$ (wherein M represents sodium, potassium or $NH_4$), or galactosyl group).

In Formula (I), $R^1$ is a hydrogen atom or a halogen atom such as chlorine, bromine or iodine atom. $R^2$ is a $C_1$–$C_6$ alkyl group such as methyl, ethyl, propyl, butyl, pentyl or hexyl group which may be straight or branched; or $C_3$–$C_6$ cycloalkyl group such as cyclopropyl, cyclobutyl, cyclopentyl or cyclohexyl. $Ar^1$ is an aromatic hydrocarbon group such as phenylene or naphthylene.

Specific examples of the preferred chemiluminescent substrates represented by Formula (I) include disodium 3-[4-methoxyspiro(1,2-dioxetane-3,2'-tricyclo[3,3,1,1$^{3,7}$]decane)-4-yl]phenyl phosphate (hereinafter also referred to as "AMPPD"); disodium 7-[4-methoxyspiro(1,2-dioxetane-3,2'-tricyclo[3,3,1,1$^{3,7}$]decane-4-yl]naphthyl-2-yl phosphate; 3-[4-methoxyspiro(1,2-dioxetane-3,2'-tricyclo[3,3,1,1$^{3,7}$]decane)-4-yl]phenyl β-D-galactopyranose; disodium 3-[4-methoxyspiro[1,2-dioxetane-3,2'-(5'-chloro)tricyclo[3,3,1,1$^{3,7}$]decane-4-yl]phenyl phosphate; and 3-[4-methoxyspiro[1,2-dioxetane-3,2'-(5'-chloro)tricyclo[3,3,1,1$^{3,7}$]decane]-4-yl]phenyl β-D-galactopyranose.

Among these, AMPPD is especially preferred in view of the fact that it is widely used in the field of clinical diagnostics.

As the chemiluminescent substrate, those represented by the following Formula (II) are also preferred.

(II)

(wherein $R^4$, $R^5$ and $R^6$ independently represent $C_1$–$C_6$ alkyl or $C_3$–$C_6$ cycloalkyl and $Ar^2$ represents a group of the following Formula (A):

(A)

(wherein $R^7$ represents a group of the formula —$OPO_3^{2-}.2M^+$ (wherein M represents sodium, potassium or $NH_4$) or galactosyl group; $R^8$ represents hydrogen, $C_1$–$C_{20}$ alkyl which may be substituted, $C_3$–$C_{20}$ cycloalkyl which may be substituted, 5- to 20-membered aryl, hydroxyl, $C_1$–$C_{20}$ alkoxy, $C_2$–$C_{20}$ alkoxyalkoxyl, $C_3$–$C_{20}$ alkoxyalkoxyalkoxyl, $C_6$–$C_{20}$ aryloxy or $C_7$–$C_{20}$ aralkyloxy; and V is oxygen or sulfur);

a group of the following Formula (B):

(B)

(wherein $R^7$ represents the same meaning as in said Formula (A); W represents C—$R^9$ ($R^9$ represents hydrogen, $C_1$–$C_{20}$ alkyl which may be substituted, $C_3$–$C_{20}$ cycloalkyl which may be substituted, 5- to 20-membered aryl, $C_1$–$C_{20}$ alkoxy, $C_2$–$C_{20}$ alkoxyalkoxyl, $C_3$–$C_{20}$ alkoxyalkoxyalkoxyl, or $C_7$–$C_{20}$ aralkyloxy); X represents oxygen or sulfur); or a group of the following Formula (C):

(wherein $R^7$ represents the same meaning as in said Formula (A); Y represents oxygen, sulfur or N—$R^{10}$; Z represents hydrogen, $C_1$–$C_{20}$ alkyl which may be substituted, $C_3$–$C_{20}$ cycloalkyl which may be substituted, 5- to 20-membered aryl, —$OR^{11}$, —$SR^{12}$ or a group of the Formula (D):

(wherein $R^{10}$ represents hydrogen, $C_1$–$C_{20}$ alkyl which may be substituted, $C_3$–$C_{20}$ cycloalkyl which may be substituted, 5- to 20-membered aryl, hydroxyl, $C_1$–$C_{20}$ alkoxyl, $C_2$–$C_{20}$ alkoxyalkoxyl or $C_3$–$C_{20}$ alkoxyalkoxyalkoxyl; $R^{11}$, $R^{12}$, $R^{13}$ and $R^{14}$ independently represent hydrogen, $C_1$–$C_{20}$ alkyl which may be substituted, $C_3$–$C_{20}$ cycloalkyl which may be substituted, or 5- to 20-membered aryl; with the proviso that (i) $R^{10}$ and $R^{11}$, (ii) $R^{10}$ and $R^{12}$, (iii) $R^{10}$ and $R^{13}$, or (iv) $R^{13}$ and $R^{14}$ may cooperatively form ring(s) that may contain not less than two hetero rings).

In the 1,2-dioxetane derivative represented by the Formula (II), $C_1$–$C_6$ alkyl may be methyl, ethyl, propyl, butyl, pentyl or hexyl which may be straight or branched, and $C_3$–$C_6$ cycloalkyl may be cyclopropyl, cyclobutyl, cyclopentyl or cyclohexyl.

In the above-described Formulae (A), (B), (C) and (D), $C_1$–$C_{20}$ alkyl which may be substituted may be a straight or branched $C_1$–$C_{20}$ non-substituted alkyl, that is, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or eicosanyl group, or a straight or branched $C_1$–$C_{20}$ alkyl such as those just mentioned above which is substituted with not less than one and not more than 5 hydroxyl groups, not less than one and not more than 5 $C_1$–$C_{20}$ alkoxyl groups, not less than one and not more than 5 $C_2$–$C_{20}$ alkoxyalkoxyl groups, not less than one and not more than 5 $C_3$–$C_{20}$ alkoxyalkoxyalkoxyl groups, and/or not less than one and not more than five 5- to 20-membered aryl group. Here, the $C_1$–$C_{20}$ alkoxyl group, $C_2$–$C_{20}$ alkoxyalkoxyl group, and $C_3$–$C_{20}$ alkoxyalkoxyalkoxyl group may be straight or branched alkoxy-containing groups such as methoxy, ethoxy, propoxy, butoxy, pentyloxy, hexyloxy, methoxyethoxy, methoxypropoxy, ethoxyethoxy, ethoxypropoxy, methoxyethoxyethoxy. The 5- to 20-membered aryl group substituting on the alkyl group may be a $C_6$–$C_{20}$ aromatic hydrocarbon group such as phenyl or naphthyl; or a 5- to 20-membered heteroaryl group containing 1 to 5 heteroatoms selected from the group consisting of nitrogen, oxygen and sulfur in ring(s), such as furyl, thienyl or pyridyl.

In Formulae (A), (B), (C) and (D), $C_3$–$C_{20}$ cycloalkyl which may be substituted may be non-substituted $C_3$–$C_{20}$ cycloalkyl, that is, cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentadecyl, cyclohexadecyl, cycloheptadecyl, cyclooctadecyl, cyclononadecyl or cycloeicosanyl group, or a $C_3$–$C_{20}$ cycloalkyl such as those just mentioned above which is substituted with not less than one and not more than 5 hydroxyl groups, not less than one and not more than 5 $C_1$–$C_{20}$ alkoxyl groups, not less than one and not more than 5 $C_2$–$C_{20}$ alkoxyalkoxyl groups, not less than one and not more than 5 $C_3$–$C_{20}$ alkoxyalkoxyalkoxyl groups, and/or not less than one and not more than five 5- to 20-membered aryl group. The above-described explanation of these substituents on the alkyl group is equally applied to the substituents on these cycloalkyl groups.

As for the $C_1$–$C_{20}$ alkoxyl, $C_2$–$C_{20}$ alkoxyalkoxyl or $C_3$–$C_{20}$ alkoxyalkoxyalkoxyl and aryl in Formulae (A), (B), (C) and (D), the above-described explanation of these substituents on the alkyl group is equally applied.

In Formulae (A), (B), (C) and (D), $C_6$–$C_{20}$ aryloxy may be, for example, phenoxy, naphthoxy or the like; and $C_7$–$C_{20}$ aralkyloxy may be, for example benzyloxy, phenetyloxy or the like.

In cases where $Ar^2$ in Formula (II) is represented by Formula (C), Y in said Formula (C) is preferably oxygen and $R^{13}$ and $R^{14}$ in Z preferably cooperatively form a 3 to 7-membered ring, more preferably, Z is a group of the following formula.

In cases where $Ar^2$ in Formula (II) is represented by Formula (C), Y may also preferably be N—$R^{10}$, Z may preferably be —$OR^{11}$, and $R^{10}$ and $R^{11}$ may preferably cooperatively form a 3 to 7-membered ring. In this case, more preferably, $R^{10}$ and $R^{11}$ form a group of the following formula:

The above-described chemiluminescent substrates may be used individually or in combination.

The amount of the chemiluminescent substrate to be used is not restricted and may be used in the range within which the chemiluminescent substrate can be dissolved in the solution subjected to the chemiluminescent assay. Usually, chemiluminescent substrate is used in a concentration in the reaction solution of 0.2 to 0.8 mg/ml.

Any known chemiluminescence enhancers which are used in chemiluminescent assays may be employed in the method of the present invention as a chemiluminescent enhancer. Preferred examples of the chemiluminescence enhancer used in the method of the present invention include TBQ, polyvinylbenzyltrimethylammonium chloride, polyvinylbenzylbenzyldimethylammonium chloride, benzyldimethylcetylammonium chloride, polymethacrylamidepropylenemethylammonium chloride, polyvinylpyrrolidone, 1,5-dimethyl-1,5-diazo-undecamethylenepolymetho bromide, polymethylene imine, poly-L-lysine and polydiallyldimethylammonium chloride. Among these chemiluminescence enhancers, polymers such as polyvinyl polymers, polymethacrylic polymer, polymethylene imine and poly-L-lysine may usually have molecular weights of about 10,000 to 1,000,000, although the molecular weights of the these polymers are not restricted thereto. Among the chemiluminescence enhancers mentioned above, TBQ is especially preferred because it has a very strong chemiluminescence-enhancing property, and is widely used as a chemiluminescence enhancer for 1,2-dioxetane compounds. These chemiluminescence enhancers may be used individually or in combination.

The amount of the chemiluminescence enhancer to be used is not restricted and may be used in the range within which the chemiluminescent enhancer can be dissolved in the solution subjected to the chemiluminescent assay. Usually, chemiluminescence enhancer is used in an concentration in the reaction solution of 0.4 to 1.6 mg/ml.

As the enzyme, acid phosphatase, alkaline phosphatase or galactosidase may preferably be employed. These enzymes may be purified from animals and plants by known methods, and also are commercially available. The commercially available enzymes may be used conveniently in the present invention.

The enzyme may be in free state or in the state of being bound to another substance such as an antigen, antibody, hapten or the like.

The chemiluminescent assay according to the present invention may be carried out in the same manner as the conventional chemiluminescent assays well-known in the art except that the above-described chemiluminescence intensity-adjusting agent co-exists in the reaction system. That is, the chemiluminescent assay may preferably be carried out at room temperature to about 40° C., more preferably at about the optimum temperature of the enzyme used. The reaction time is not restricted and may usually be 1 minute to 60 minutes, preferably 3 minutes to 20 minutes. The reaction medium may be a buffer solution such as PBS appropriate for the enzyme reaction as in the conventional chemiluminescent assays, of which pH may preferably be near the optimum pH of the enzyme used. The chemiluminescence from the reaction product can be measured by using a well-known and commercially available photocounter as in the conventional chemiluminescent assays.

In the chemiluminescent assay according to the present invention, it is necessary to carry out the chemiluminescent assay in the presence of the above-described chemiluminescence intensity-adjusting agent. By virtue of the chemiluminescence intensity-adjusting agent, the efficiency of enhancement of the chemiluminescence intensity by the chemiluminescence enhancer is made to be substantially constant irrespective of the concentration of the enzyme, so that the relationship between the enzyme concentration and the intensity of the emitted chemiluminescence is close to the proportional or linear relationship. It should be noted that the chemiluminescence intensity-adjusting agent serves to make the relationship between the enzyme concentration and the intensity of the emitted chemiluminescence closer to the proportional relationship by somewhat reducing the chemiluminescence intensity, and does not increase the chemiluminescence intensity.

The chemiluminescent assay according to the present invention may be applied to any of the fields to which the conventional chemiluminescent assays are applied. Among the fields, enzyme immunoassay is an important field. Enzyme immunoassay per se is well-known in the art. In enzyme immunoassay, an enzyme is used as a label or marker bound to an antigen, antibody, hapten or the like, and the enzyme is detected or quantified employing the enzyme reaction by which the chemiluminescent substrate comes to emit chemiluminescence or to change the intensity of the chemiluminescence. Use of chemiluminescent assay in enzyme immunoassay is well-known in the art. For example, in a typical sandwich ELISA (enzyme-linked immunosorbent assay) which is a representative example of enzyme immunoassays, a first antibody is immobilized on a solid phase and an antigen to be quantified which is specific to the first antibody is reacted with the first antibody. After washing, a second antibody which is labeled with an enzyme, which antibody is specific to the antigen is reacted with the captured antigen. After washing, the captured second antibody, that is, the captured enzyme is quantified utilizing the chemiluminescent assay. It should be noted that the sandwich ELISA just mentioned above is merely an example and sandwich ELISA or enzyme immunoassay is not restricted to the example.

In enzyme immunoassay, the target substance which is to be detected or quantified is not restricted at all, and may be, for example, antigens such as hormones, enzymes, proteins, cytokines, bacterial cells, viruses and the like as well as antibodies to these antigens. The sample to be subjected to the enzyme immunoassay is also not restricted at all, and may be, for example, body fluids such as bloods, plasmas, sera, urine and tissue fluids; and foods and beverages.

In the immunoassay, the antibody may be either a polyclonal antibody or a monoclonal antibody, and the latter is preferred in view of the specificity. Monoclonal antibodies may be prepared by a conventional method according to Kohler and Milstein (Nature, 256, 495 (1975)). The prepared antibody may be purified by a conventional method. The purified antibody may be used as it is or after fragmentation to an antigen-binding fragment such as Fab fragment or $F(ab')_2$ fragment.

The invention will now be described in more detail by way of examples thereof.

COMPARATIVE EXAMPLE 1

α-fetoprotein (AFP) as an antigen was quantified by a two-step sandwich enzyme immunoassay using magnetic particles to which a monoclonal anti-AFP antibody is bound as the solid phase, and alkaline phosphatase (hereinafter also referred to as "ALP")-bound monoclonal anti-AFP antibody as a labeled antibody as follows:

An aqueous substrate solution containing 0.2 mg/ml of AMPPD as the chemiluminescent substrate, 0.4 mg/ml of TBQ as the chemiluminescence enhancer, 0.1 M diethanolamine (DEA), 1 mM magnesium chloride and 0.05% sodium azide ($NaN_3$) (pH 10.0) was prepared.

Samples containing 0, 10, 100, 800 and 2000 ng/ml of AFP, respectively, were diluted with 10 times volume of BSA solution. Twenty microliters aliquot of each of these solutions was added to 250 μl of 0.015 wt % suspension of the anti-AFP antibody-bound magnetic particles and, after stirring, each of the reaction mixtures was allowed to react in a reaction vessel at 37° C. for 10 minutes. Then the reaction vessel was contacted with a magnet to collect the magnetic particles, and the collected magnetic particles were washed. Then 250 μl of 0.1 μg/ml ALP-bound anti-AFP antibody solution was added to the particles and the resulting mixture was allowed to react at 37° C. for 10 minutes. Then the reaction vessel was contacted with a magnet to collect the magnetic particles, and the collected magnetic particles were washed. To the washed particles, 200 μl of the above-described substrate solution was added and mixed.

Figure 1:
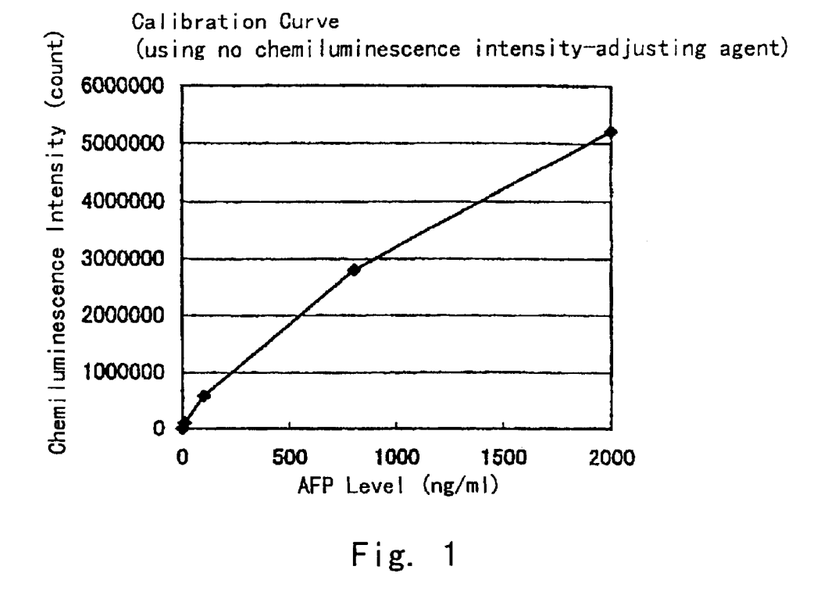
FIG. 1 shows a calibration curve obtained in Comparative Example 1 wherein a chemiluminescence intensity-adjusting agent was not used.

The reaction mixture was allowed to react at 37° C. for 5 minutes and the intensity of the emitted chemiluminescence was measured with a photocounter. The obtained calibration curve is shown in FIG. 1.

EXAMPLE 1

The same procedure as in Comparative Example 1 was repeated except that the substrate solution contained 0.08 mg/ml or 0.16 mg/ml of MTAB as a chemiluminescence intensity-adjusting agent.

Figure 2:
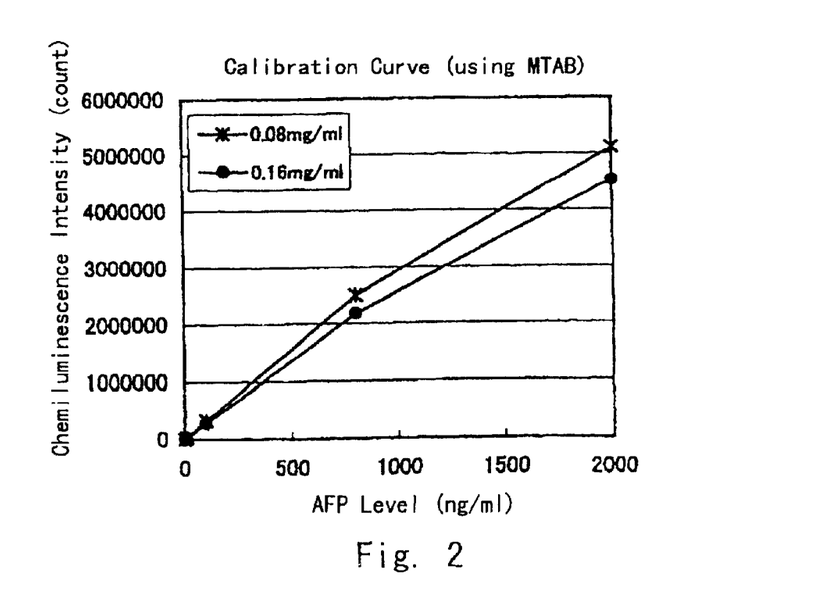
FIG. 2 shows calibration curves obtained in Example 1 wherein different concentrations of MTAB was used as the chemiluminescence intensity-adjusting agent.
Figure 3:
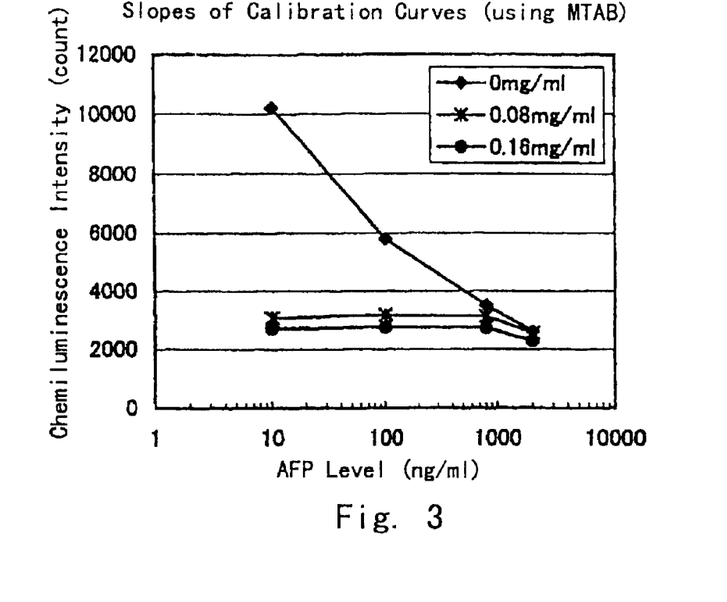
FIG. 3 shows the relationship between the AFP level and the slope of each calibration curve obtained in Example 1 or Comparative Example 1.

The obtained calibration curves are shown in FIG. 2. The relationship between the AFP level and the slope of each calibration curve is shown in FIG. 3. In FIG. 3, the results of Comparative Example 1 are also shown.

As seen from FIG. 3, the slopes of the calibration curves obtained in Example 1 in which MTAB was used as a chemiluminescence intensity-adjusting agent were almost constant while that obtained in Comparative Example 1 apparently changes depending on the AFP level. This clearly indicates that according to the present invention, the relationship between the enzyme concentration and the intensity of the emitted chemiluminescence is close to proportional relationship while that obtained in the conventional method which does not use the chemiluminescence intensity-adjusting agent is not.

EXAMPLE 2

Figure 4:
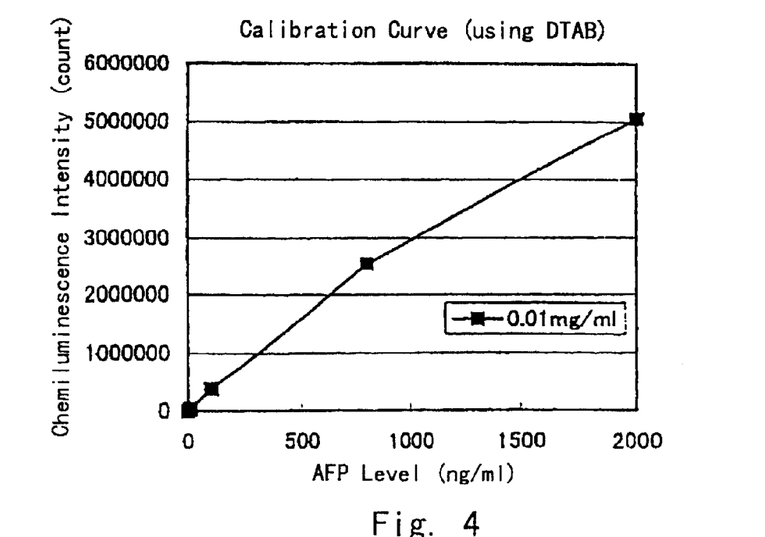
FIG. 4 shows a calibration curve obtained in Example 2 wherein DTAB was used as the chemiluminescence intensity-adjusting agent.

The same procedure as in Example 1 was repeated except that the substrate solution contained 0.01 mg/ml DTAB as the chemiluminescence intensity-adjusting agent in place of MTAB. The results are shown in FIG. 4.

EXAMPLE 3

Figure 5:
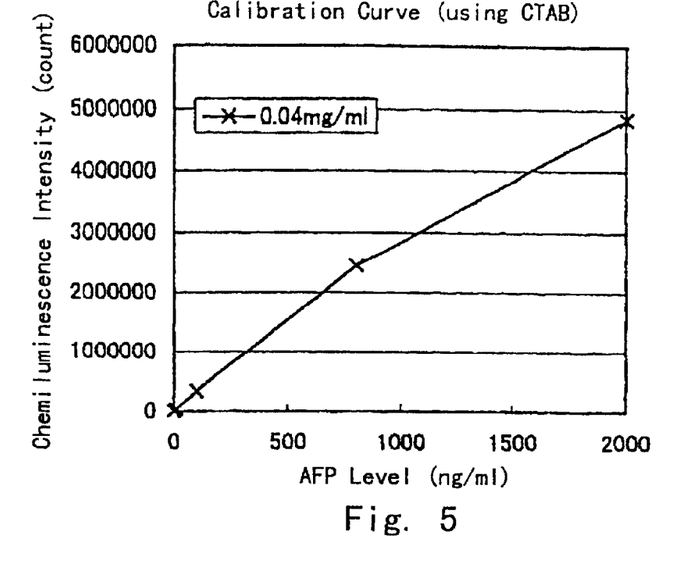
FIG. 5 shows a calibration curve obtained in Example 3 wherein CTAB was used as the chemiluminescence intensity-adjusting agent.

The same procedure as in Example 1 was repeated except that the substrate solution contained 0.04 mg/ml CTAB as the chemiluminescence intensity-adjusting agent in place of MTAB. The results are shown in FIG. 5.

EXAMPLE 4

Figure 6:
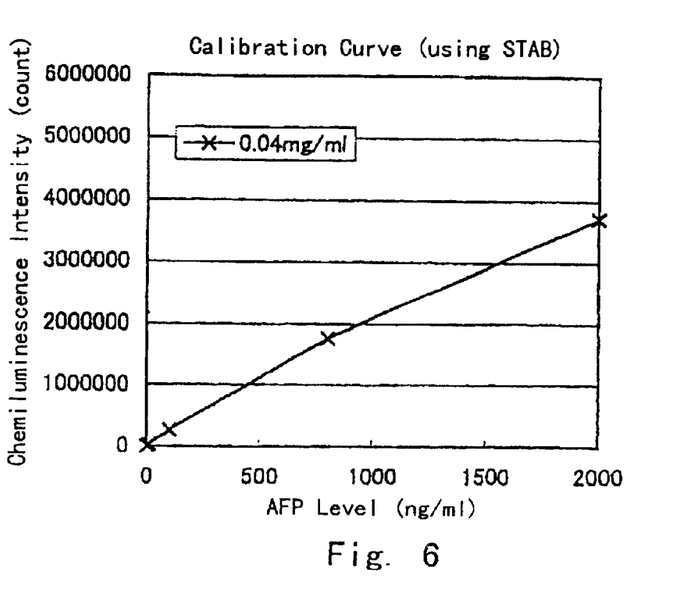
FIG. 6 shows a calibration curve obtained in Example 4 wherein STAB was used as the chemiluminescence intensity-adjusting agent.

The same procedure as in Example 1 was repeated except that the substrate solution contained 0.04 mg/ml STAB as the chemiluminescence intensity-adjusting agent in place of MTAB. The results are shown in FIG. 6.

EXAMPLE 5

Figure 7:
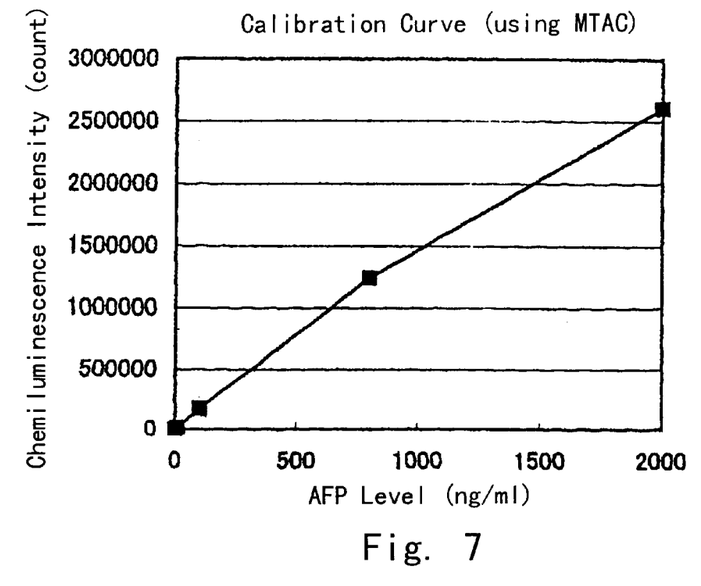
FIG. 7 shows a calibration curve obtained in Example 5 wherein MTAC was used as the chemiluminescence intensity-adjusting agent.

The same procedure as in Example 1 was repeated except that the substrate solution contained 0.08 mg/ml MTAC as the chemiluminescence intensity-adjusting agent in place of MTAB. The results are shown in FIG. 7.

EXAMPLE 6

Figure 8:
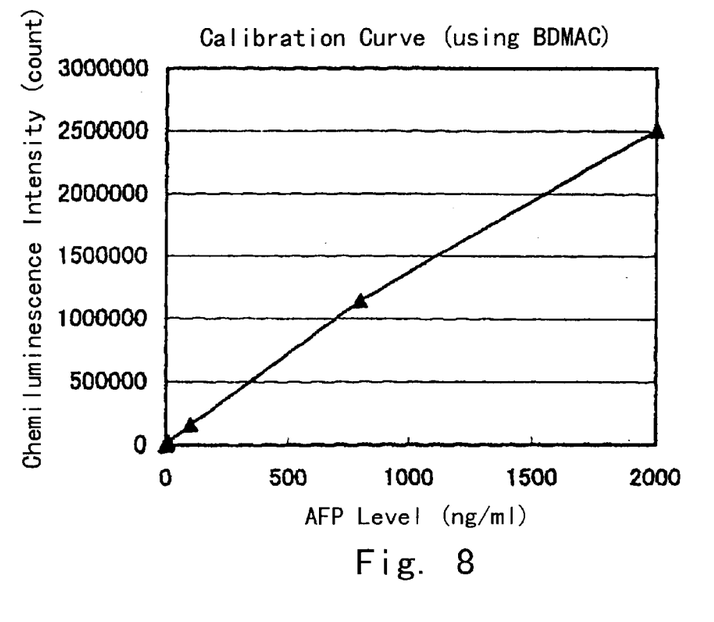
FIG. 8 shows a calibration curve obtained in Example 6 wherein BDMAC was used as the chemiluminescence intensity-adjusting agent.

The same procedure as in Example 1 was repeated except that the substrate solution contained 0.08 mg/ml BDMAC as the chemiluminescence intensity-adjusting agent in place of MTAB. The results are shown in FIG. 8.

EXAMPLE 7

Figure 9:
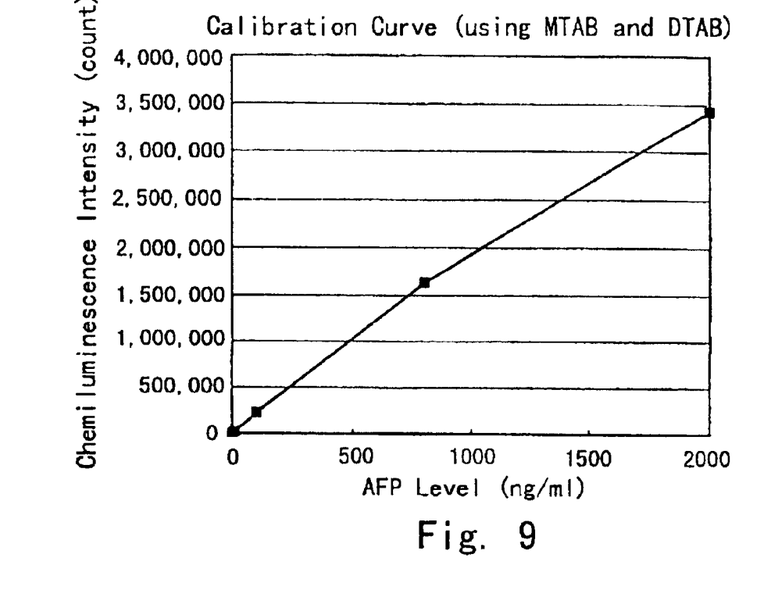
FIG. 9 shows a calibration curve obtained in Example 7 wherein MTAB and DTAB were used as the chemiluminescence intensity-adjusting agent.

The same procedure as in Example 1 was repeated except that the substrate solution contained 0.04 mg/ml MTAB and 0.04 mg/ml DTAB as the chemiluminescence intensity-adjusting agent. The results are shown in FIG. 9.

EXAMPLE 8

Figure 10:
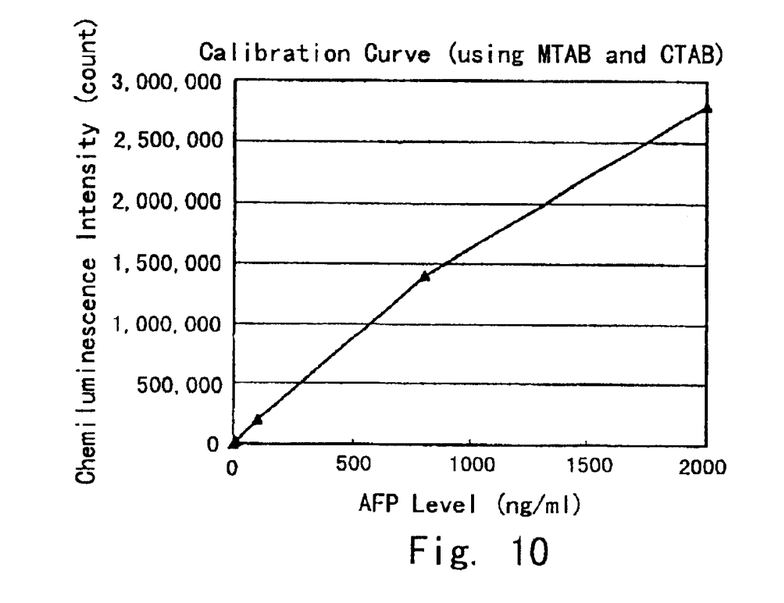
FIG. 10 shows a calibration curve obtained in Example 8 wherein MTAB and CTAB were used as the chemiluminescence intensity-adjusting agent.

The same procedure as in Example 1 was repeated except that the substrate solution contained 0.04 mg/ml MTAB and 0.04 mg/ml CTAB as the chemiluminescence intensity-adjusting agent. The results are shown in FIG. 10.

EXAMPLE 11

Figure 11:
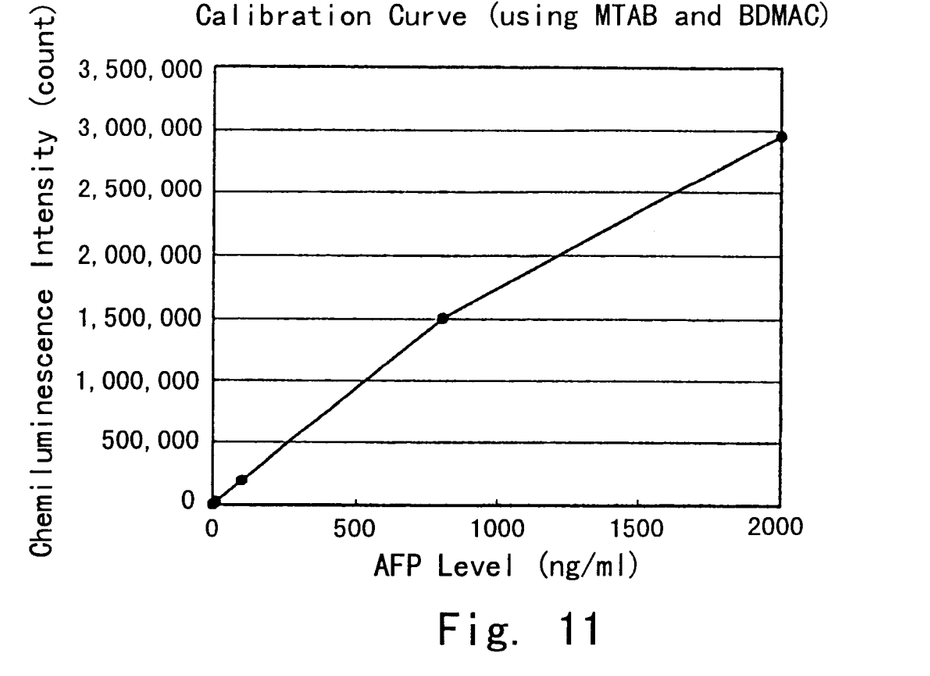
FIG. 11 shows a calibration curve obtained in Example 9 wherein MTAB and BDMAC were used as the chemiluminescence intensity-adjusting agent.

The same procedure as in Example 1 was repeated except that the substrate solution contained 0.04 mg/ml MTAB and 0.04 mg/ml BDMAC as the chemiluminescence intensity-adjusting agent. The results are shown in FIG. 11.

We claim:

1. A chemiluminescent assay comprising subjecting a chemiluminescent substrate to an enzyme reaction in the presence of the enzyme carrying out said enzyme reaction, a chemiluminescence enhancer and a chemiluminescence intensity-adjusting agent selected from the group consisting of myristyltrimethylammonium bromide, lauryltrimethylammonium bromide, stearyltrimethylammonium bromide, myristyltrimethylammonium chloride and benzyldimethylmyristylammonium chloride; and measuring resulting chemiluminescence from reaction product.

2. The method according to claim 1, wherein said chemiluminescence intensity-adjusting agent is myristyltrimethylammonium bromide.

3. The method according to any claim 1, wherein concentration of said chemiluminescent substrate is 0.2 to 0.8 mg/ml, concentration of said chemiluminescence enhancer is 0.4 to 1.6 mg/ml, and weight of said chemiluminescence intensity-adjusting agent is $1/40$ to the same of the weight of said chemiluminescence enhancer.

4. The method according to claim 3, wherein the weight of said chemiluminescence intensity-adjusting agent is $1/5$ to $1/2$ of the weight of said chemiluminescence enhancer.

5. The method according to claim 1, wherein said chemiluminescent substrate is a, 1,2-dioxetane derivative of the following Formula (I):

(I)

(wherein $R^1$ represents hydrogen or halogen; $R^2$ represents $C_1$–$C_6$ alkyl or $C_3$–$C_6$ cycloalkyl; $Ar^1$ represents phenylene or naphthylene; $R^3$ represents a group of the formula —$OP_3^{2-}$.$2M^+$ (wherein M represents sodium, potassium or $NH_4$), or galactosyl group).

6. The method according to claim 5, wherein $R^1$ is hydrogen and $Ar^3$ is 3-phenylene group.

7. The method according to claim 6, wherein $R^2$ is methyl and $R^3$ is —$OPO_3^{2-}$.$2Na^+$.

8. The method according to claim 1, wherein said chemiluminescent substrate is represented by the following Formula (II):

(II)

(wherein $R^4$, $R^5$ and $R^6$ independently represent $C_1$–$C_6$ alkyl or $C_3$–$C_6$ cycloalkyl and $Ar^2$ represents a group of the following Formula (A):

(A)

(wherein $R^7$ represents a group of the formula —$OPO_3^{2-}$·$2M^+$ (wherein M represents sodium, potassium or $NH_4$) or galactosyl group; $R^8$ represents hydrogen, $C_1$–$C_{20}$ alkyl which may be substituted, $C_3$–$C_{20}$ cycloalkyl which may be substituted, 5- to 20-membered aryl, hydroxyl, $C_1$–$C_{20}$ alkoxy, $C_2$–$C_{20}$ alkoxyalkoxyl, $C_3$–$C_{20}$ alkoxyalkoxyalkoxyl, $C_6$–$C_{20}$ aryloxy or $C_7$–$C_{20}$ aralkyloxy; and V is oxygen or sulfur);

a group of the following Formula (B):

(B)

(wherein $R^7$ represents the same meaning as in said Formula (A); W represents C—$R^9$ ($R^9$ represents hydrogen, $C_1$–$C_{20}$ alkyl which may be substituted, $C_3$–$C_{20}$ cycloalkyl which may be substituted, 5- to 20-membered aryl, $C_1$–$C_{20}$ alkoxy, $C_2$–$C_{20}$ alkoxyalkoxyl, $C_3$–$C_{20}$ alkoxyalkoxyalkoxyl or $C_7$–$C_{20}$ aralkyloxy); X represents oxygen or sulfur); or a group of the following Formula (C):

(C)

(wherein $R^7$ represents the same meaning as in said Formula (A); Y represents oxygen, sulfur or N—$R^{10}$; Z represents hydrogen, $C_1$–$C_{20}$ alkyl which may be substituted, $C_3$–$C_{20}$ cycloalkyl which may be substituted, 5- to 20-membered aryl, —$OR^{11}$, —$SR^{12}$ or a group of the Formula (D):

(D)

(wherein $R^{10}$ represents hydrogen, $C_1$–$C_{20}$ alkyl which may be substituted, $C_3$–$C_{20}$ cycloalkyl which may be substituted, 5- to 20-membered aryl, hydroxyl, $C_1$–$C_{20}$ alkoxyl, $C_2$–$C_{20}$ alkoxyalkoxyl, $C_3$–$C_{20}$ alkoxyalkoxyalkoxyl; $R^{11}$, $R^{12}$, $R^{13}$ and $R^{14}$ independently represent hydrogen, $C_1$–$C_{20}$ alkyl which may be substituted, $C_3$–$C_{20}$ cycloalkyl which may be substituted, or 5- to 20-membered aryl; with the proviso that (i) $R^{10}$ and $R^{11}$, (ii) $R^{10}$ and $R^{12}$, (iii) $R^{10}$ and $R^{13}$, or (iv) $R^{13}$ and $R^{14}$ may cooperatively form ring(s) that may contain not less than two hetero rings).

9. The method according to claim 8, wherein Y in said Formula (C) is oxygen and $R^{13}$ and $R^{14}$ in Z cooperatively form a 3 to 7-membered ring.

10. The method according to claim 9, wherein Z in said Formula (C) is a group of the following formula 11. The method according to claim 8, wherein in said Formula (C), Y is N—$R^{10}$, Z is —$OR^{11}$, and $R^{10}$ and $R^{11}$ cooperatively form a 3 to 7-membered ring.

12. The method according to claim 11, wherein the ring cooperatively formed by $R^{10}$ and $R^{11}$ in said Formula (C) is a group of the following formula 13. The method according to claim 8, wherein in said Formulae (A), (B), (C) and (D), said $C_1$–$C_{20}$ alkyl which may be substituted is a $C_1$–$C_{20}$ non-substituted alkyl group or a $C_1$–$C_{20}$ alkyl group which is substituted with not less than one and not more than 5 hydroxyl groups, not less than one and not more than 5 $C_1$–$C_{20}$ alkoxyl groups, not less than one and not more than 5 $C_2$–$C_{20}$ alkoxyalkoxyl groups, not less than one and not more than 5 $C_3$–$C_{20}$ alkoxyalkoxyalkoxyl groups and/or not less than one and not more than five 5- to 20-membered aryl group; said $C_3$–$C_{20}$ cycloalkyl which may be substituted is a $C_3$–$C_{20}$ non-substituted cycloalkyl group or a $C_3$–$C_{20}$ cycloalkyl group which is substituted with not less than one and not more than 5 hydroxyl groups, not less than one and not more than 5 $C_1$–$C_{20}$ alkoxyl groups, not less than one and not more than 5 $C_2$–$C_{20}$ alkoxyalkoxyl groups, not less than one and not more than 5 $C_3$–$C_{20}$ alkoxyalkoxyalkoxyl groups and/or not less than one and not more than five 5- to 20-membered aryl group; and said 5- to 20-membered aryl group in said Formulae (A), (B), (C) and (D) is a $C_6$–$C_{20}$ aromatic hydrocarbon group or a 5- to 20-membered heteroaryl group containing 1 to 5 heteroatoms selected from the group consisting of nitrogen, oxygen and sulfur in ring(s).

14. The method according to claim 1, wherein said chemiluminescence enhancer is at least one selected from the group consisting of polyvinylbenzyltributylammonium chloride, polyvinylbenzyltrimethylammonium chloride, polyvinylbenzylbenzyldimethylammonium chloride, benzyldimethylcetylammonium chloride, polymethacrylamidepropylenemethylammonium chloride, polyvinylpyrrolidone, 1,5-dimethyl-1,5-diazo-undecamethylenepolymetho bromide, polymethylene imine, poly-L-lysine and polydiallyldimethylammonium chloride.

15. The method according to claim 14, wherein said chemiluminescence enhancer is polyvinylbenzyltributylammonium chloride.

16. The method according to claim 1, wherein said enzyme is acid phosphatase, alkaline phosphatase or galactosidase.

17. The method according to claim 1, wherein said method is conducted in an enzyme immunoassay.

* * * * *